| United States Patent [19] | [11] Patent Number: 4,900,412 |
| Ker et al. | [45] Date of Patent: Feb. 13, 1990 |

[54] HEATED SOLID ELECTROLYTE OXYGEN SENSOR HAVING UNIQUE HEATER ELEMENT

[75] Inventors: Eric L. Ker, Grand Blanc, Mich.; Theodore R. Vasilow, Monroeville, Pa.

[73] Assignee: General Motors Corporation, Detroit, Mich.

[21] Appl. No.: 235,420

[22] Filed: Aug. 24, 1988

[51] Int. Cl.⁴ ............................................. G01N 27/58
[52] U.S. Cl. ..................................... 204/427; 204/408
[58] Field of Search ............... 204/408, 410, 411, 421, 204/425, 426, 427, 428, 429

[56] References Cited

U.S. PATENT DOCUMENTS

| 3,844,920 | 10/1974 | Burgett et al. | 204/426 |
| 4,282,080 | 8/1981 | Muller et al. | 204/426 |
| 4,395,319 | 7/1983 | Torisu et al. | 204/429 X |
| 4,507,191 | 3/1985 | Ebizawa et al. | 204/408 X |
| 4,512,871 | 4/1985 | Kato et al. | 204/428 X |
| 4,528,086 | 7/1985 | Kato et al. | 204/429 X |
| 4,540,479 | 9/1985 | Sakurai et al. | 204/427 |
| 4,560,463 | 12/1985 | Frey et al. | 204/428 X |
| 4,578,174 | 3/1986 | Kato et al. | 204/429 |
| 4,636,293 | 1/1987 | Bayha et al. | 204/427 X |
| 4,639,305 | 1/1987 | Shibata et al. | 204/408 X |
| 4,657,660 | 4/1987 | Sato et al. | 204/29 X |

OTHER PUBLICATIONS

U.S. Ser. No. 110,353, "Heated Solid Electrolyte Oxygen Sensor" to Ker et al., filed Oct. 19, 1987.

Primary Examiner—Nam X. Nguyen
Attorney, Agent, or Firm—Domenica N. S. Hartman

[57] ABSTRACT

A readily manufacturable heated solid electrolyte oxygen sensor. A heater subassembly readily adaptable to unheated oxygen sensor technology, provides a greater reference oxygen gas source to the reference electrode of the solid electrolyte body, in addition to being positioned and rigidly secured within the oxygen sensing device.

4 Claims, 2 Drawing Sheets

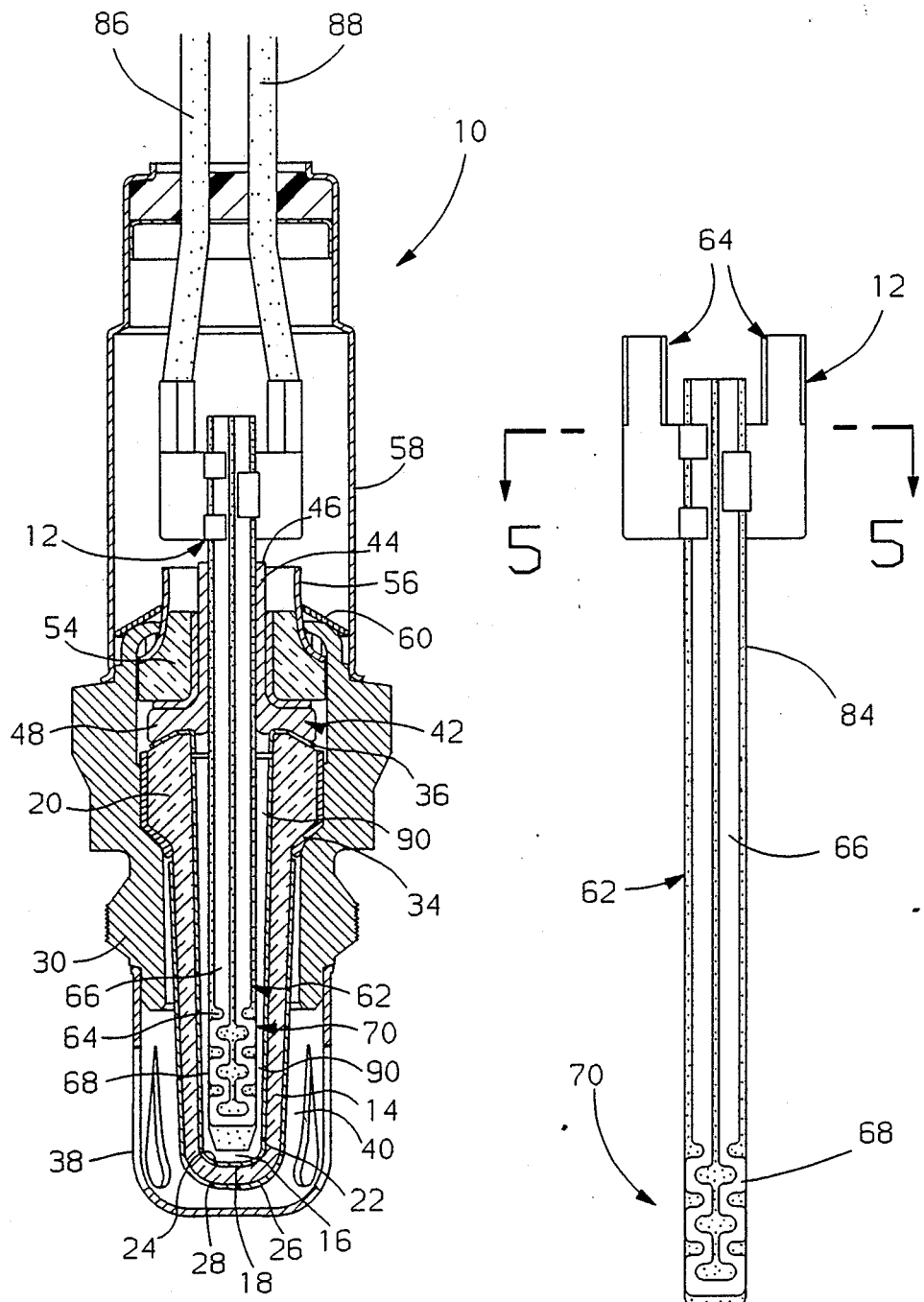

HEATED SOLID ELECTROLYTE OXYGEN SENSOR HAVING UNIQUE HEATER ELEMENT

The present invention generally relates to an electrochemical type solid electrolyte oxygen sensor suitable for detecting oxygen concentrations in automotive exhaust emitted from an internal combustion engine. More specifically, this invention relates to a self-heating oxygen sensor of this type having a unique heater element, which is rugged, durable and readily assembleable.

BACKGROUND OF THE INVENTION

Gas sensors are employed in a variety of applications requiring qualitative and quantitative gaseous determinations. In the automotive industry, it is well known that the oxygen concentration in the automobile exhaust has a direct relationship to the engine air-to-fuel ratio. Oxygen gas sensors are employed within the automobile internal combustion control system to provide accurate exhaust gas oxygen concentration measurements for determination of optimum combustion conditions, maximization of efficient fuel usage, and management of exhaust emissions.

Generally, the electrochemical type of oxygen sensor employed in automotive applications utilizes a thimble shaped electrochemical galvanic cell to determine, or sense, the relative amounts of oxygen present in the exhaust stream, an example being U.S. Pat. No. 3,844,920 to Burgett et al. This type of oxygen sensor is generally known and used throughout the automotive industry, and comprises an ionically conductive solid electrolyte material, typically yttria stabilized zirconia, a porous electrode coating on the exterior exposed to the exhaust or measuring gas and a porous electrode coating on the interior exposed to a known concentration of reference gas. The gas concentration gradient across the solid electrolyte produces a galvanic potential which is related to the differential of the partial pressures of the gas at the two electrodes by the Nernst equation: $E = AT \ln[P_1/P_2]$, where E is the galvanic voltage, T is the absolute temperature of the gas, $P_1/P_2$ is the ratio of the partial pressures of the reference gas at the two electrodes, and $A = R/4F$, where R is the universal gas constant and F is the Faraday constant. Thus, the oxygen sensor senses the oxygen concentration in the exhaust gas by measuring this galvanic output voltage.

As evidenced by the above recitation of the Nernst equation, sensor galvanic output voltage is dependent on temperature. In addition, the solid electrolyte member comprised within an oxygen sensor must first be heated to an elevated temperature in order to obtain an appreciable output voltage in response to the difference in the oxygen concentrations between the reference and measuring electrodes. The induced galvanic potential between electrodes and corresponding output voltage are not stable until the solid electrolyte has been heated to a given temperature. In general, the conventional oxygen sensors which do not have means for self-heating, rely on the combustion gases to heat the solid electrolyte of the oxygen sensor to an operating temperature sufficient to effect galvanic stability. Effective sensor operation is therefore delayed until the combustion gases reach an appropriate elevated temperature so as to thereby heat the solid electrolyte within the sensor to the appropriate operational temperature.

Also, if the sensor is placed too far downstream in the exhaust pipe of an engine, especially a highly efficient engine, the sensor may not be heated to a high enough temperature during engine idle to meet sensor specifications. During these conditions, the internal combustion engine control system operates open loop, i.e., the control system does not sense the controlled parameter, air-to-fuel ratio, in order to control that parameter. It is known that a large percentage of the total emissions produced are produced during this period of engine warm up. Therefore, in some applications, emissions control during engine warm up might be improved with an oxygen sensor which had means for rapidly heating itself to a predetermined temperature, regardless of the temperature of the surrounding environment.

Further, it is known that temperatures of the combustion gases from an internal combustion engine vary widely during operation, up to about a few hundred degrees Centigrade. Therefore another advantage of a self-heating oxygen sensor is that it may be positioned anywhere in the automobile exhaust pipe since the solid electrolyte of the sensor is not dependent on the heat of the combustion gases for raising its temperature. The heated oxygen sensor could be located at the cooler exit end of the exhaust pipe, which is significantly less degrading to the physical and chemical properties of the sensor than being disposed at the hot end of the exhaust pipe.

In summary, there is strong motivation to provide an oxygen sensor capable of heating itself. Many heated oxygen sensors have been proposed in the art. These prior heated oxygen sensors generally comprise an elongated ceramic heater which positively heats the solid electrolyte body of the sensor. The heater element is typically inserted into an elongated cylindrical hole formed in the solid electrolyte body. An example of a prior heated oxygen sensor of this type is U.S. Ser. No. 110,353 to Ker et al, now U.S. Pat. No. 4,824,500, entitled "Heated Solid Electrolyte Oxygen Sensor", which is assigned to the same assignee of this patent application.

For automotive applications particularly, a heated oxygen sensor should be rugged, reliable, and readily manufacturable at a low cost. It is also desirable that the heater components be readily adaptable to the current oxygen sensor design and manufacturing techniques. Therefore, it is highly desirable to provide a heater element for a heated oxygen sensor which is easy to fabricate, can be built at minimal cost, and provides a rugged, reliable assembly. Lastly, it is preferable that the heater element be readily incorporated into conventional unheated oxygen sensors typified by the above mentioned U.S. Pat. No. 3,844,920 to Burgett et al.

SUMMARY OF THE INVENTION

It is an object of the present invention to provide an improved heated solid electrolyte electrochemical oxygen sensor, the improved heated oxygen sensor being durable and reliable in operation, even in comparatively varying environmental conditions.

It is a further object of this invention that such improved heated oxygen sensor have a unique heater element.

It is still a further object of this invention that such improved heated oxygen sensor and heater element be adaptable to conventional unheated oxygen sensor technology and readily amenable to automotive production techniques.

In accordance with the preferred embodiment of this invention, these and other objects and advantages are accomplished as follows.

According to the present invention, there is provided a heated oxygen sensing device suitable for detecting oxygen concentrations in automotive exhaust emitted from an internal combustion engine, which provides a greater reference oxygen gas source to the reference electrode on the inner surface of the solid electrolyte body.

The oxygen sensing device comprises a solid electrolyte body, a housing, an elongated heater element, and self-aligning means for rigidly securing and centering the elongated heater element within the solid electrolyte body. The solid electrolyte body is substantially tubular and has an elongated bore located axially, with a first end closed by the solid electrolyte body and a second end open. A reference electrode is provided on the inner surface of the solid electrolyte body. A measuring electrode which contacts the exhaust gas to be measured is provided on the outer surface of the solid electrolyte body. The housing supports the solid electrolyte body so that the measuring electrode on the outer surface of the solid electrolyte body contacts the exhaust gas, while the reference electrode on the inner surface of the solid electrolyte body is gas tight to the external exhaust gas.

The elongated heater element is inserted into the elongated bore within the solid electrolyte body. The heater element and solid electrolyte body are securely positioned using self-aligning means, so that a gap is provided everywhere therebetween the solid electrolyte body and elongated heater element. The elongated heater element comprises a heating resistor having a positive temperature coefficient of resistance and a ceramic body carrying the heating resistor. The heater element is contacted at a fixed number of points, permitting greater air flow around the solid electrolyte body and heater element, which in turn provides a greater reference oxygen gas source to the reference electrode on the inner surface of the solid electrolyte body. This is an advantage not realized by circular heater elements common in the prior art.

According to a preferred aspect of this invention, the heater element has a rectangular cross section and comprises an alumina core, thick film resistance heating platinum conductors and an overlaying insulating layer.

The present invention describes a novel concept for providing a heated oxygen sensor having a novel ceramic rod heater. This heated oxygen sensor is easy to fabricate, may be built at minimal cost, and provides a rugged, reliable sensor assembly. Further, the heater subassembly is readily incorporated into conventional unheated oxygen sensors typified by the above mentioned U.S. Pat. No. 3,844,920 to Burgett et al or the heated oxygen sensor described in U.S. Pat. No. 4,824,550 to Ker et al, both of which are assigned to the same assignee of the patent application.

Other objects and advantages of this invention will be better appreciated from the following detailed description.

BRIEF DESCRIPTION OF THE DRAWINGS

FIG. 1 is a cross sectional view of a heated solid electrolyte oxygen sensor in accordance with a preferred embodiment of this invention and illustrates the solid electrolyte body, housing and heater element.

FIG. 2 is a plan view of the heater subassembly having the heater element in accordance with a preferred embodiment of this invention.

DETAILED DESCRIPTION OF THE INVENTION

Figures 3, 4:
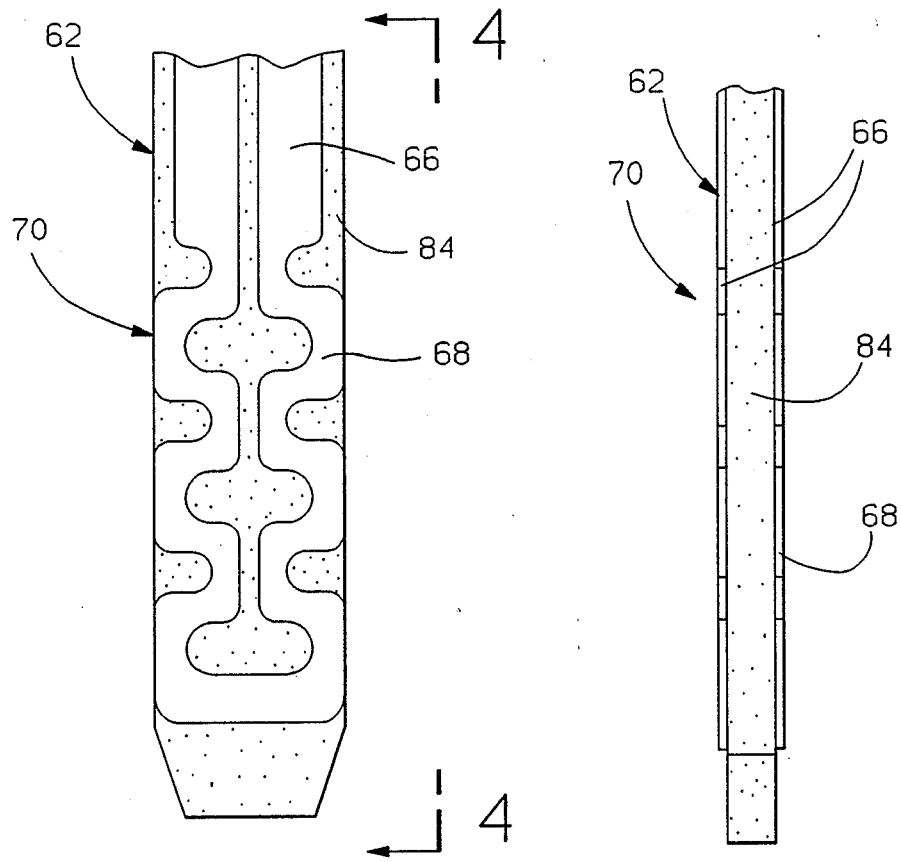
FIG. 3 is an enlarged view of the convoluted region of the platinum conductor shown in FIG. 2.
FIG. 4 is a side view of the heater element in accordance with a preferred embodiment of this invention as shown in FIG. 1.

This invention results in a heated, solid electrolyte, electrochemical oxygen sensing device suitable for detecting oxygen partial pressures of exhaust gases emitted from an internal combustion engine, which is rugged, reliable, readily assembleable, and amenable to automotive production techniques.

In the preferred embodiment of this invention, the heated oxygen sensing device 10, as shown in FIG. 1, comprises a heater subassembly 12, as shown in FIG. 2, within an oxygen sensing device. The solid electrolyte body 14 comprises yttria stabilized zirconia and is substantially tubular having an elongated bore 16 located axially. The first end 18 of the solid electrolyte body 14 is closed by the solid electrolyte material. The second end 20 of the solid electrolyte body 14 is open, so that the heater subassembly 12 may be inserted into the elongated bore 16 of the solid electrolyte body 14. A reference electrode 22, preferably comprising porous platinum, is provided on the inner surface 24 of the solid electrolyte body 14 in the elongated bore 16 and contacts a known concentration of reference gas. A measuring electrode 26, preferably comprising porous platinum, is provided on the outer surface 28 of the solid electrolyte body 14 and contacts the exhaust gas to be measured.

The housing 30 is adapted to fit into the exhaust pipe of the automobile, typically by the use of mounting plates (not shown). The housing 30 supports the solid electrolyte body 14 so that the measuring electrode 26 on the outer surface 28 of the solid electrolyte body 14 contacts the external exhaust gas to be measured, while keeping the reference electrode 22 on the inner surface 24 of the solid electrolyte body 14 gas tight to the external exhaust gas. The solid electrolyte body 14 is mounted so as to resemble a finger-like projection into the flow of exhaust gases. Lower and intermediate gaskets 34 and 36, respectively, seal the elongated bore 16 of the solid electrolyte body 14 and prevent flow of the external exhaust gas into the elongated bore 16 of the solid electrolyte body 14 where the reference electrode 22 is provided. A perforated shield 38 is attached to the housing 30 and provides protection for the solid electrolyte body 14. A gap 40 is provided between the perforated shield 38 and solid electrolyte body 14 to allow uninterrupted flow of the exhaust gases through the perforated shield 38 to the porous platinum measuring electrode 26 on the outer surface 28 of the solid electrolyte body 14.

A stop body 42 having a tubular extension 44 at a first end 46 of the stop body 42 is concentric with the elongated bore 16 of the solid electrolyte body 14. The second end 48 of the stop body 42 is shaped to adapt to the intermediate gasket 36. The stop body 42 may be formed from any suitable material, preferably a 400 series stainless steel. The stop body 42 provides a self-aligning means for securely positioning the heater subassembly 12 during subsequent fabrication of the heated sensor 10.

An alumina insulator 54 is positioned by the stop body 42 and insulates the metal stop body 42 from the housing 30 and inner upper shield 56, which are both also preferably formed from a metal. The galvanic output signal generated between the reference and measuring electrodes 22 and 26, flows through the intermediate gasket 36 and stop body 42 to the external measuring electronics (not shown); therefore the alumina insulator 54 is required to prevent extraneous electrical communication of this output signal to the housing 30 or inner upper shield 56.

An outer upper shield 58 is held by a spring clip 60, or other suitable means, to the inner upper shield 56. The outer upper shield 58 and inner upper shield 56 provide additional protection for the heated oxygen sensor 10 and may be formed from a suitable material.

FIG. 2 is a plan view of the heater subassembly 12 having a heater element 62 in accordance with a preferred embodiment of this invention. The heater subassembly 12, which is readily adaptable to conventional unheated oxygen sensor design, as shown in FIG. 2, comprises electrical contacts and an elongated heater element 62. An inventive feature of the present invention resides in the elongated heater element 62.

The elongated heater element 62 is contacted by two metal clips 64 for electrical contact to form the heater subassembly 12, as shown in FIG. 2. The heater element 62 is electrically connected by the metal clips 64 to a heater power wire 86 and ground wire 88. The elongated heater element 62 comprises a heating resistor 66, having a positive coefficient of resistance overlaying a ceramic base 84.

In the preferred embodiment, the heating resistor 66 is provided by thick film conductors which have been screen printed and patterned onto the ceramic base 84, preferably an alumina ceramic. The thick film heater element 62 utilizes a ceramic base 84 material, such as the alumina, with overlaying printed resistant heater ink. The ceramic base 84 may be a single layer or a lamination of two or more layers. The green form of the ceramic base may be formed by tape casting to produce a single layer or multi-layer base having a rectangular cross-section, or by roll compacting and pressing for forming a single layer base with various cross sectional shapes such as rectangular, pentagonal, or triangular. The resistance heating ink, which is preferably platinum although other suitable materials such as palladium, silver, gold or tungsten may also be used, is subsequently printed onto one side or both sides of the ceramic surface 84. Alternatively, the resistance heating ink may be printed on an underlying layer and subsequently covered by an overlaying layer of the ceramic, therefore sandwiched between intermediate layers of the ceramic base. Other suitable methods for depositing the resistance heating ink onto the ceramic base 84 may also be used.

The preferred embodiment for the elongated heater element 62 has a rectangular cross section for ease of manufacturability and comprises an alumina base 84, thick film platinum positive resistance heating wires 66 on two opposite faces of the ceramic base 84, and an overlaying blanket layer of an insulative material such as alumina or glass, which is not shown for clarity.

An inventive feature of the present invention is that the resistance heating wires 66 is patterned so as to be convoluted 68 at an end of the heater element 62; the end of the heater element 62 which will subsequently be inserted into the closed end 20 of the solid electrolyte body 14 in the region 40 where the solid electrolyte body 14 contacts the exhaust gases to be measured. The convolutions 68 define the primary heating zone 70 of the heater element 62. The convolutions 68 may extend throughout the entire length of the heater element 62, however it is preferable that they be located only in the region 70 where heating is desirable, such as only the region which extends into that portion of the solid electrolyte body 14 which contacts the exhaust gases to be measured; i.e., approximately the last 20 percent of the heater element 62. With this configuration, only the necessary regions of the sensor 10 are heated, thereby avoiding the heating of any unnecessary or unduly massive components. Suitable results are also obtained when the convolutions 68 extend upward on the heater element 62 into the housing 30. FIG. 3 shows an exploded view of the heating zone 70 where the convolutions 68 are disposed and FIG. 4 shows a side view of that same heating zone 70.

In addition, it is preferred that the resistance heating 66 material have a positive coefficient of resistance. Therefore, as the temperature of the heater element 62 is increased, it becomes increasingly difficult to raise the temperature of the heater element 62, thereby allowing the exhaust gases to heat the element 62 and sensor 10. A positive coefficient of resistance of about 0.3 %/°C. is preferable, although the coefficient may range between about 0.1–0.5 %/°C. without significant detrimental effects to the oxygen sensor 10.

Figure 5:
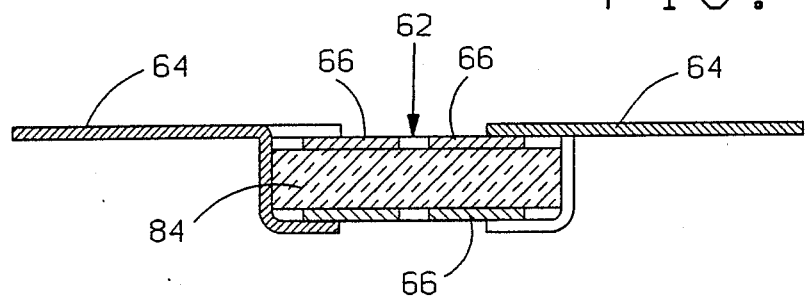
FIG. 5 is an enlarged cross-sectional view through the heater subassembly in accordance with a preferred embodiment of this invention.

The elongated heater element 62 is contacted by two metal clips 64, preferably by crimping or other suitable means, for electrical contact to form the heater subassembly 12, as shown in FIG. 2. The heater element 62 is electrically connected by the metal clips 64 to a heater power wire 86 and ground wire 88. A cross section through the electrical contacts 64 and heater element 62 is shown in FIG. 5. As shown in FIG. 5, in the preferred embodiment, the metal clips 64 contact both thick film platinum resistance heating wires 66. The heater subassembly 12 comprising the heater element 62, electrical contact clips 64, power and ground wires 86 and 88, is inserted into the stop body 42 and secured using an interference fit between the heater element 62 and stop body 42. The interference fit securely positions the heater element 62 within the solid electrolyte body 14 in a radial, orbital and longitudinal direction.

An advantage of utilizing a heater element 62 having a non-circular cross section, is that the stop body 42 only contacts the heater element 62 at a fixed number of points, permitting greater air flow between the stop body 42 and heater element 62, which in turn provides a greater reference oxygen gas source to the reference electrode 22 on the inner surface 24 of the solid electrolyte body 14. This is an advantage not realized by circular heater elements common in the prior art. This aspect of the present invention provides some flexibility in the heated oxygen sensor design, a desirable feature for any component in the automotive industry.

The heater element 62 is positioned within the stop body 42 so that an appropriate length of the heater element 62 projects into the elongated bore 16 of the solid electrolyte body 14 when the heater subassembly 12 is inserted into the elongated bore 16 of the solid electrolyte body 14. A gap 90 is desired everywhere between the heater element 62 and solid electrolyte body 14 in order to ensure a constant reference oxygen source to the reference electrode 22 and also to prevent any detrimental overheating of the solid electrolyte body 14 or porous platinum reference electrode 22. Alternatively, it is also desirable to optimally minimize the gap 90 between the heater element 62 and solid electrolyte body 14 in order to quickly achieve uniform heating throughout the solid electrolyte body 14. As noted in FIGS. 1-4 the tip of the heater element 62 is preferably tapered so as to ensure a reasonable gap 90 everywhere between the heater element 62 and solid electrolyte body 14.

A desirable feature of the present invention is that the heater element 62 is contacted at only a fixed number of points, permitting greater air flow between the stop body 42 and heater element 62, which in turn provides a greater reference oxygen gas source to the reference electrode 22 on the inner surface 24 of the solid electrolyte body 14. A further desirable feature of the present invention is its amenability to automotive mass production techniques. The heater subassembly 12 is relatively easy to assemble and may be utilized in conventional unheated oxygen sensors without much modification of the conventional design. The heater subassembly 12 when installed in the stop body 42 of the housing 30 is self-aligning and rigidly secured in all directions of movement. In addition, this heater subassembly is readily adaptable to the heated oxygen sensor and gripping body described in U.S. Ser. No 110,353 wherein the gripping body securely positions the heater subassembly in all directions within the solid electrolyte body and electrically communicates the galvanic output voltage to the external measuring electronics.

While our invention has been described in terms of a preferred embodiment, it is apparent that other forms could be adopted by one skilled in the art. Accordingly, the scope of our invention is to be limited only by the following claims.

The embodiments of the invention in which an exclusive property or privilege is claimed are defined as follows:

1. An oxygen sensing device, comprising:

a substantially tubular solid electrolyte body having an elongated bore centrally and axially located, with a first end closed by said solid electrolyte body and a second end open, said solid electrolyte body having a reference electrode provided on an inner surface thereof and a measuring electrode provided on an outer surface thereof;

a housing, said housing supports said solid electrolyte body so that said measuring electrode of said solid electrolyte body contacts the external gas to be measured and so that said reference electrode of said solid electrolyte body is gas tight to the external gas to be measured; and an elongated rod-like heater element having a substantially non-circular cross section defined by a polygon, and comprising an alumina base and a heating resistor having a positive coefficient of resistance, said heating resistor is convoluted in at least one region so as to provide a primary heating portion of said heater element in said convoluted region, said elongated heater element being inserted within said elongated bore of said solid electrolyte body so that said convoluted region of said heating resistor is located at an end of said heater element which extends into said solid electrolyte body; and self-aligning means for rigidly securing at a plurality of non-continuous points defined by said polygonal cross section and centering said elongated heater element within said solid electrolyte body so that a gap exists everywhere therebetween said heater element and said solid electrolyte body, while also electrically coupling the galvanic output signal generated between said reference electrode and said measuring electrode to external electronic measuring equipment.

2. An oxygen sensing device according claim 1 wherein said heating resistor comprises thick film platinum.

3. An oxygen sensing device according to claim 1 wherein said heating resistor comprises palladium, silver, gold or tungsten.

4. An oxygen sensing device according to claim 1 wherein said elongated heater element is characterized by a rectangular cross section.

* * * * *